United States Patent [19]
Jones

[11] Patent Number: 5,237,854
[45] Date of Patent: Aug. 24, 1993

[54] UNSTEADY-STATE PROFILE PERMEAMETER - METHOD AND APPARATUS

[75] Inventor: Stanley C. Jones, Littleton, Colo.
[73] Assignee: Western Atlas International, Inc., Houston, Tex.
[21] Appl. No.: 873,458
[22] Filed: Apr. 24, 1992
[51] Int. Cl.⁵ .................................... G01N 15/08
[52] U.S. Cl. ................................................ 73/38
[58] Field of Search ...................................... 73/38

[56] References Cited

U.S. PATENT DOCUMENTS

| | | |
|---|---|---|
| 2,867,116 | 1/1959 | Aronofsky et al. .................. 73/38 |
| 3,405,553 | 10/1968 | Boisard et al. ..................... 73/38 |
| 4,537,063 | 8/1985 | Barnaby ............................ 73/38 |
| 4,627,270 | 12/1986 | Jones ............................... 73/38 |
| 5,157,960 | 10/1992 | Brehm et al. ...................... 73/38 |

Primary Examiner—Hezron E. Williams
Assistant Examiner—Joseph W. Roskos
Attorney, Agent, or Firm—Elizabeth W. Layman

[57] ABSTRACT

"A method and apparatus for automated, non-destructive permeability determination of a whole-core reservoir rock sample from pressure and time measurements taken as a known volume of pressurized gas, injected into the sample through a probe, diffuses through the sample in a modified hemispherical flow pattern.

25 Claims, 8 Drawing Sheets

UNSTEADY-STATE PROFILE PERMEAMETER - METHOD AND APPARATUS

FIELD OF THE INVENTION

The present invention relates to a method and apparatus for use in determining attributes such as permeability. More specifically, the invention pertains to a non-steady-state, non-destructive technique for measuring the permeability of core samples of reservoir rock.

BACKGROUND OF THE INVENTION

Permeability is the capacity of a porous material, such as reservoir rock, to transmit fluids (the fluid conductivity of a rock). It is one of the most important parameters in determining the rate of fluid flow in a reservoir. Detailed permeability measurements on slabbed or unslabbed whole cores are especially useful for interpretation of geologically complex, heterogeneous formations.

The concept of using "probe permeameters" for non-destructive measurements of permeability is well known. One such device is made by Edinburgh Petroleum Services. These prior art probe permeameters utilize a steady-state technique.

A small diameter tube, or probe, is pushed against the surface of a core sample cut from the reservoir. The end of this probe is fitted with a rubber gasket or O-ring, which makes a gas-tight seal between the sample and the probe. Air or nitrogen is delivered from the probe through the interior of the seal to the rock sample at a fixed, measured pressure. The gas then diffuses through the rock sample, starting from the spot beneath the seal, diverging in a somewhat hemispherical pattern and ultimately passing from the upper surface of the sample just beyond the outer diameter of the gasket or O-ring, and from other surfaces of the sample that are exposed to atmospheric pressure.

The flowrate and pressure of the gas delivered from the probe is measured directly using devices such as a mass flow meter or rotameter and a pressure transducer or pressure gauge. When the flowrate and pressure become constant (invariant with time), "steady state" is achieved. The upstream, delivered pressure and flowrate are then recorded and the permeability is calculated. A variant of this prior art, steady-state procedure consists of holding the upstream, delivered flowrate constant by means of a flow controller. When the upstream, delivered pressure becomes invariant with time, steady-state conditions are attained and the measurements are made.

One disadvantage of the steady-state measurements is the long period of time that elapses before steady-state conditions are reached. The wait time to reach steady-state increases as the permeability of the core material decreases. It reaches twenty minutes or more for low permeability samples. Another drawback is the need for directly measuring the flowrate. Most flowrate measuring devices have a very limited range with accuracy only reaching about ±1%.

The range of permeabilities that can be measured by existing commercial probe permeameters is claimed to be from about 0.1 millidarcys (md) to about 10,000 md. Measurements of permeabilities below about 5 md, however, can have a large percentage error.

SUMMARY OF THE INVENTION

The present invention is a method and apparatus for determining the permeability of reservoir rock. The present invention employs a transient, pressure-decay technique that directly measures time intervals and changes in pressure of a gas as it flows from a reservoir of accurately known volume into a core sample. The technique then determines the flowrate indirectly from the volume and pressure-time parameters and calculates the permeability of the core sample based on instantaneous flowrates and upstream pressures. The technique increases the range of permeabilities that can be measured. The method and apparatus determine Klinkenberg permeability and the effective (non-slip corrected) gas permeability.

BRIEF DESCRIPTION OF THE DRAWING FIGURES

DETAILED DESCRIPTION OF THE INVENTION

First Preferred Embodiment

Figure 1:
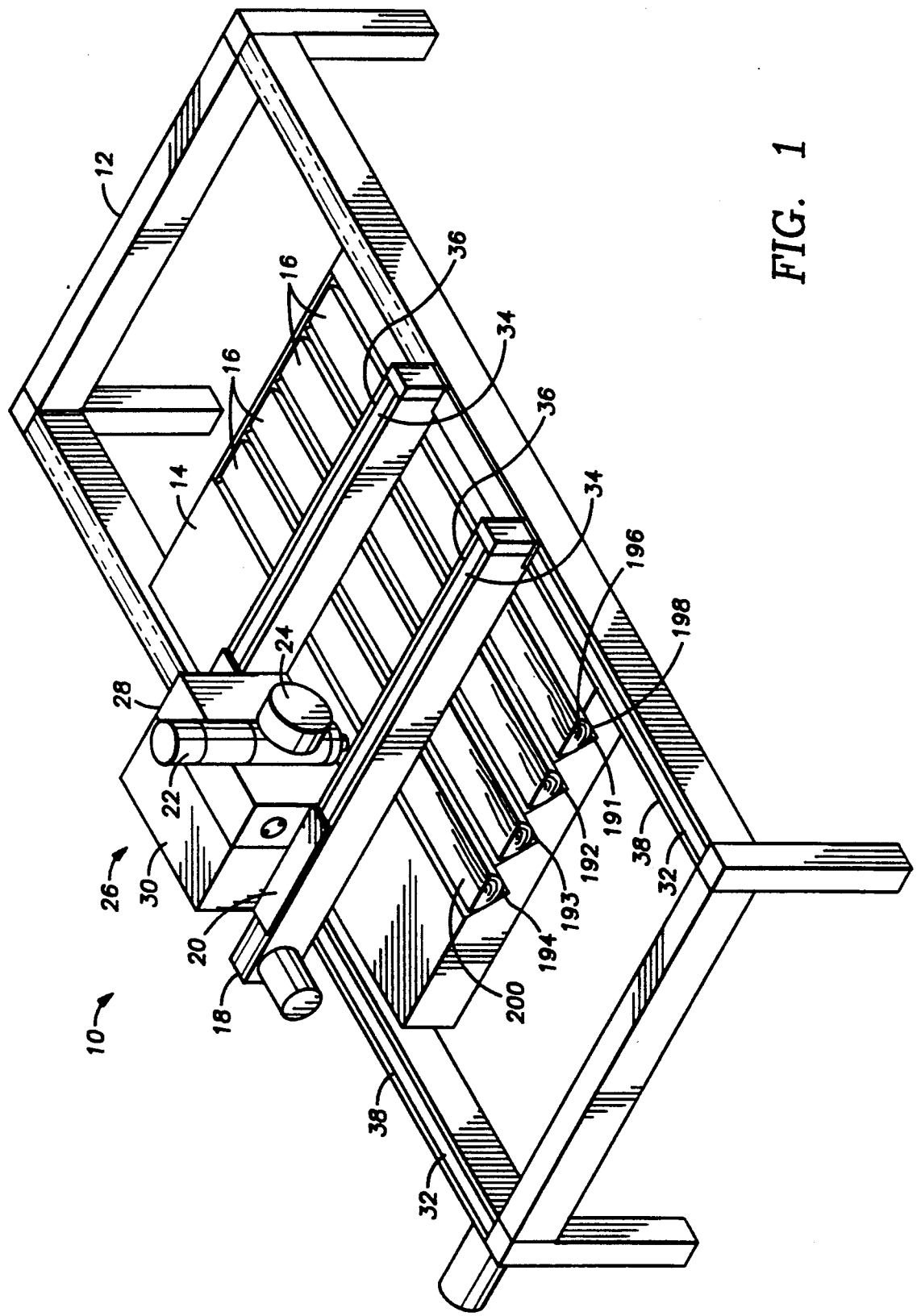
FIG. 1 is a perspective view of one preferred embodiment of the invention.

FIG. 1 illustrates a first preferred embodiment of a probe permeameter 10. The permeameter 10 comprises a table 12, a core rack 14 mounted on the table 12 for holding core sample(s) 16, an x-carriage 18 and a y-carriage 20 for positioning a probe 22 to a desired position above the core sample 16, a pressure transducer 24, a reservoir system 26 which includes a manifold 28 and a large-tank container 30 and a control system (not shown). The control system for the permeameter 10 is a computer (not shown).

The operator places a core sample 16 in a first channel 191 of the core rack 14. The core sample 16 is positioned such that an upper end 196 of the core sample 16 is towards a channel edge 198 of the first channel 191. If the core sample 16 is slabbed, it is placed with a plane surface 200 facing upward.

A slabbed core sample is preferred to ensure a proper seal between the probe 22 and the slabbed surface 200 of the core sample 16. To prepare a slabbed core, a portion of core is removed, usually with a diamond-studded saw, leaving a flat surface 200 on the core. Often the "upper" one-third of the core sample 16 is removed. "Upper" refers to the top portion of the core sample 16 when the core sample 16 is lying with its axis in a horizontal position. The slabbed surface 200 provides a better seal due to its flatness which conforms to the flat bottom of the probe 22.

To insure a proper seal with an unslabbed, whole core sample (not shown), the probe 22 is positioned directly above the axis of the core sample 16 and fitted with a compliant probe tip (not shown) to compensate for the curvature of the whole core. The calculation of permeability is based on the probe 22 being sealed against a planar upper boundary of the core sample 16 but one of ordinary skill in the art could adapt the calculation for a curved surface.

Once the core sample 16 is in position, the operator inputs the reference depth to the computer for each core sample 16 in the core rack 14 that is to be measured. When the core sample 16 is cut into core sample lengths, the reservoir depth at which the core sample 16 was taken from the earth usually is written on the core sample 16 and a line is drawn perpendicular to the axis of the core sample 16 to indicate the specific line on the core sample 16 corresponding to that depth. There is normally at least one such reservoir depth mark for each one meter of core.

The table 12 in the permeameter 10 is sectioned into x and y coordinates which are measured from the front left corner of the table 12. The operator manually positions the probe 22 until it is directly above the leading edge (closest to the operator) of the reference depth line on the core sample 16 to be tested. This is accomplished by moving the y-carriage 20 forward or backward along y-rails 36 and the x-carriage 18 laterally along x-rails 38 until the probe 22 is in the desired position.

Figure 2:
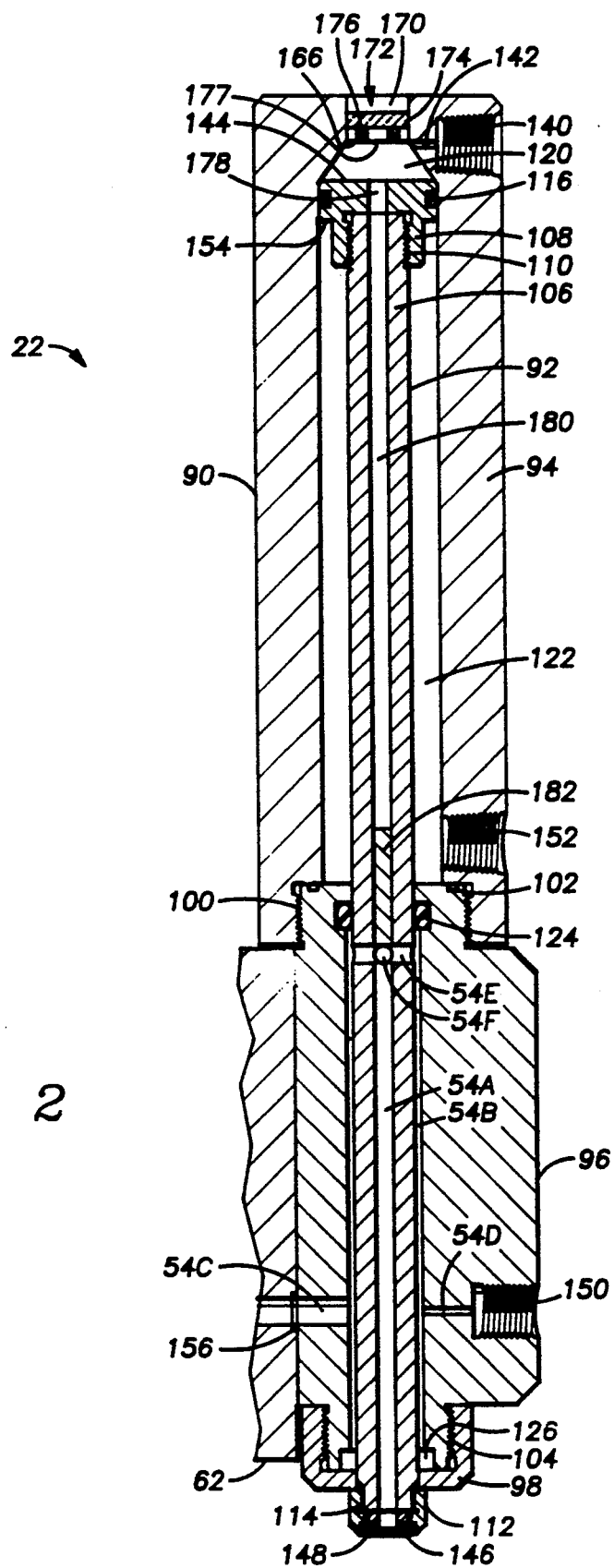
FIG. 2 is a cross-sectional view of the probe.

Positioning of the probe 22 in the permeameter 10 is facilitated by the use of a laser light 170 (shown in FIG. 2). A laser energy source (not shown) energizes the laser light 170 which is located at the top of an upper-cylindrical housing 94 of the probe 22. A laser-light housing 172 in the permeameter 10 is a cylinder approximately one inch in length which is attached to and recessed in the top of the upper-cylindrical housing 94 along the axis of the probe 22. A plane glass lens 174, such as made by Edmonds Scientific, is placed at the bottom of the laser-light housing 172 beneath the laser light 170. The lens 174 is placed against an O-ring 176 which is seated in a groove surrounding an aperture 177 leading to an upper chamber 120 of the upper-cylindrical housing 94 to provide a seal between the laser-light housing 172 and the upper chamber 120. The resultant light beam follows a path through the glass lens 174, the aperture 177, the upper chamber 120, an aperture 178 in an operator piston 108, an axial hole 180 through the center of a probe rod 106, a Plexiglas plug 182 at the bottom of the axial hole 180 and portions of a probe chamber 54 in a lower-cylindrical housing 96 and exits at the bottom of the probe 22. The light appears as a small red dot on the core sample 16 and indicates the exact position on the core sample 16 where the centerline of the probe 22 would touch if lowered.

When the probe 22 is properly positioned, the operator pushes a button (not shown) to signal the computer that the probe 22 is positioned above the reference point for this core sample 16. The computer then inputs position data from an x-position sensor 32 and a y-position sensor 34. Although the permeameter 10 employs x and y-position sensors 32 and 34, other position-determining methods, such as a stepper motor and drive screw (not shown), can be employed.

The computer stores the x and y data for the reference point of this core sample 16. The x-coordinate represents the reference depth and the y-coordinate represents the edge of the core sample 16 closest to the front of the table 12. If the probe 22 is moved to the right along the x-rails 38 (FIG. 1), the computer will add the distance moved to the reference point to determine the depth because this part of the core would be from a point deeper within the reservoir than the reference point of the core sample 16. Movement to the left represents core from a shallower depth.

The y reference point represents the leading edge of the core sample 16 which is closest to the front of the core rack 14 towards the operator. If the probe 22 is moved further away from the operator along the y-rails 36, the computer adds that distance to the y reference point because the probe 22 is now positioned further into the core. The maximum y value for this core sample would be the width of the slabbed portion of the core sample 16.

In a similar manner, the operator "shows" the computer the upper end 196 and bottom end (not shown) of each core sample 16 in the core rack 14 and the start and end points of any portions of the core sample(s) 16 that are to be skipped because of rubble, vugs or other undesirable condition.

Figure 3:
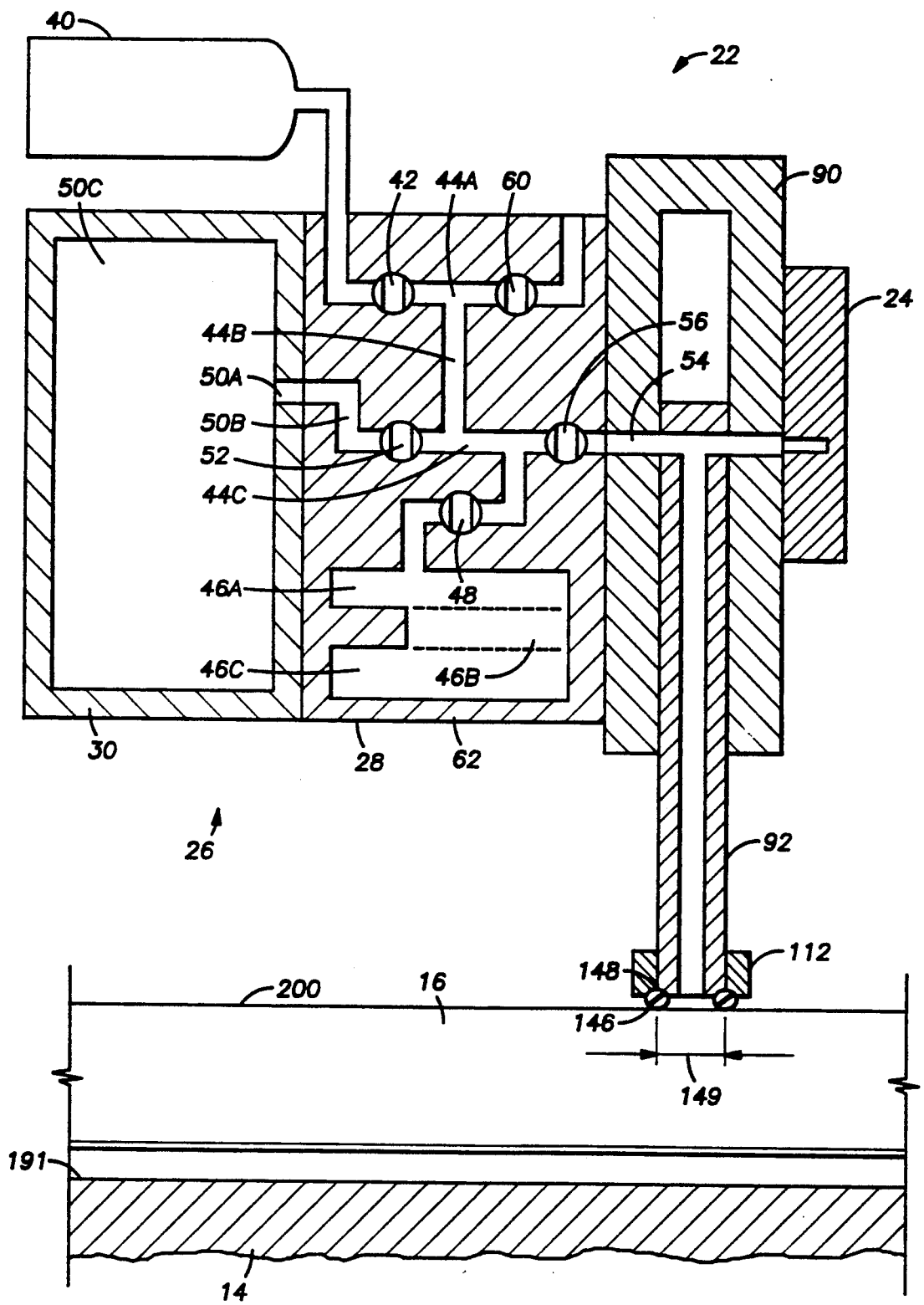
FIG. 3 is a schematic of the reservoir system and probe.

FIG. 3 is a schematic of the probe 22 and the reservoir system 26 which, in the preferred embodiment permeameter 10, have four gas-containment chambers of accurately known volumes. The chambers in the preferred embodiment can be calibrated by a Boyle's Law technique in which gas, at a known pressure in a reference cell (not shown) of accurately known volume, is expanded into each chamber to be calibrated. After expansion into a chamber, the pressure of the gas is measured and the volume of that chamber is calculated from the known pressure at the start of the expansion, the measured pressure after the expansion and the known volume of the reference cell.

A pressurized gas supply 40 provides gas to the reservoir system 26 and the probe 22 through a fill valve 42. The gas used in the permeameter 10 is nitrogen but could be other gases such as air or helium. The gas fills a manifold chamber 44 (shown as 44A-C), a small-tank chamber 46 (shown as 46A-C) through a sm valve 48, a large-tank chamber 50 (shown as 50A-C) through a large-tank valve 52 and the probe chamber 54 through a probe valve 56. The pressure transducer 24 measures the pressure of the gas in the probe chamber 54 when the probe chamber 54 is in sealed communication with the core sample 16. A vent valve 60, connected to the manifold chamber 44, is provided to allow the reservoir system 26 to be initialized to ambient pressure and for calibration of the pressure transducer 24 and for calibration of the chambers 44, 46, 50 and 54.

The approximate capacities of the four gas-containment chambers in this permeameter 10 are 720 cc for the large-tank chamber 50, 120 cc for the small-tank chamber 46, 20 cc for the manifold chamber 44 and 4 cc for the probe chamber 54. This arrangement of the reservoir system 26 is designed such that the shut off of each gas-containment chamber from the largest to the smallest results in a reduction of the remaining volume by a factor of six. Correspondingly, the rate of the pressure decay is increased by a factor of six because it is inversely proportional to the total connected volume in the reservoir system 26 and the probe 22.

Figure 4:
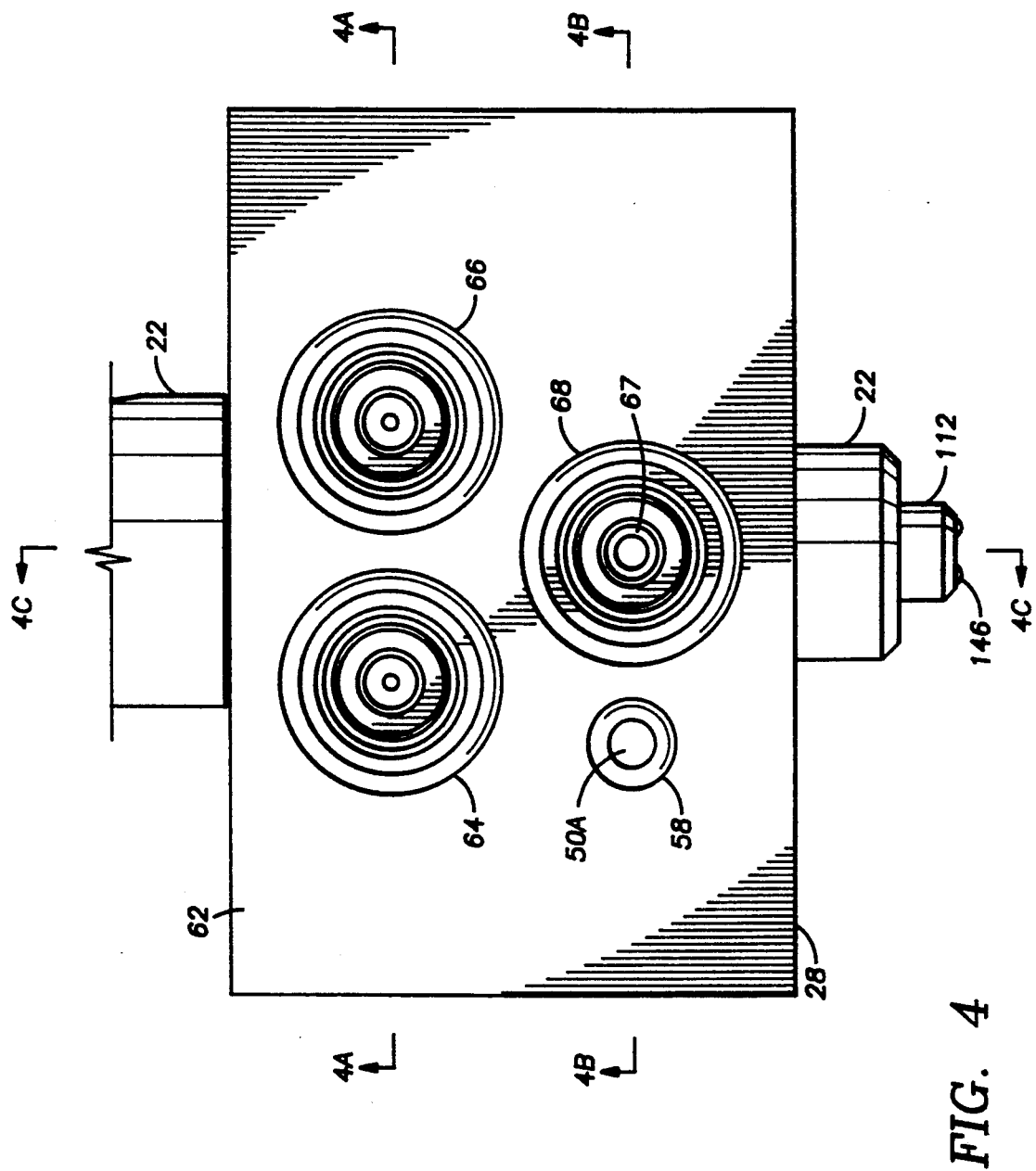
FIG. 4 is a back view of the manifold portion of the reservoir system.

The manifold 28 in the permeameter 10 consists of a manifold block 62 which has been machined to form various cavities, gas-containment chambers and channels as described below. As shown in FIG. 4, the back view of the manifold block 62 when separated from the large-tank container 30 reveals a vent-valve cavity 64, a fill-valve cavity 66 a probe-valve cavity 68 and a large-tank inlet 50A sealed by an O-ring 58. The manifold block 62 in the preferred embodiment is made of aluminum but this is only by way of example and is not meant to exclude other acceptable materials such as brass. The material is chosen for its heat capacity and heat conductivity characteristics as explained below.

Figure 4A:
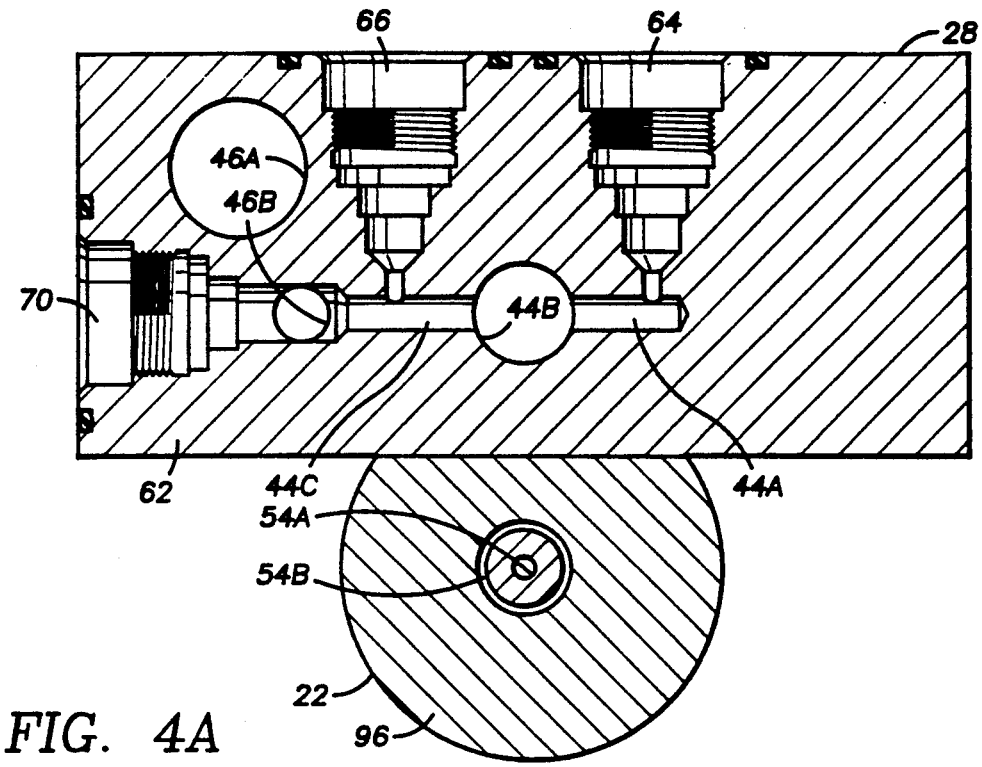
FIG. 4A is a sectional view along line A-A' of FIG. 4 through the vent-valve and fill-valve cavities.

FIG. 4A is a cross-sectional view along line A-A' of FIG. 4 through the upper portion of the manifold block 62. It shows the vent-valve cavity 64, the fill-valve cavity 66, a small-tank-valve cavity 70, a probe inner-volume 54A, a probe outer-volume 54B and the three parts of the manifold chamber 44: a vent channel 44A, a central manifold bore 44B and a small-tank channel 44C. The small-tank chamber 46 in the permeameter 10 consists of three parts: an upper portion 46A, a middle portion 46B and a lower portion 46C (shown in FIG. 4B). The number of parts comprising the small-tank chamber 46 and the shapes and interrelationships of these parts are shown for example only and are not meant to exclude other configurations.

Figure 4B:
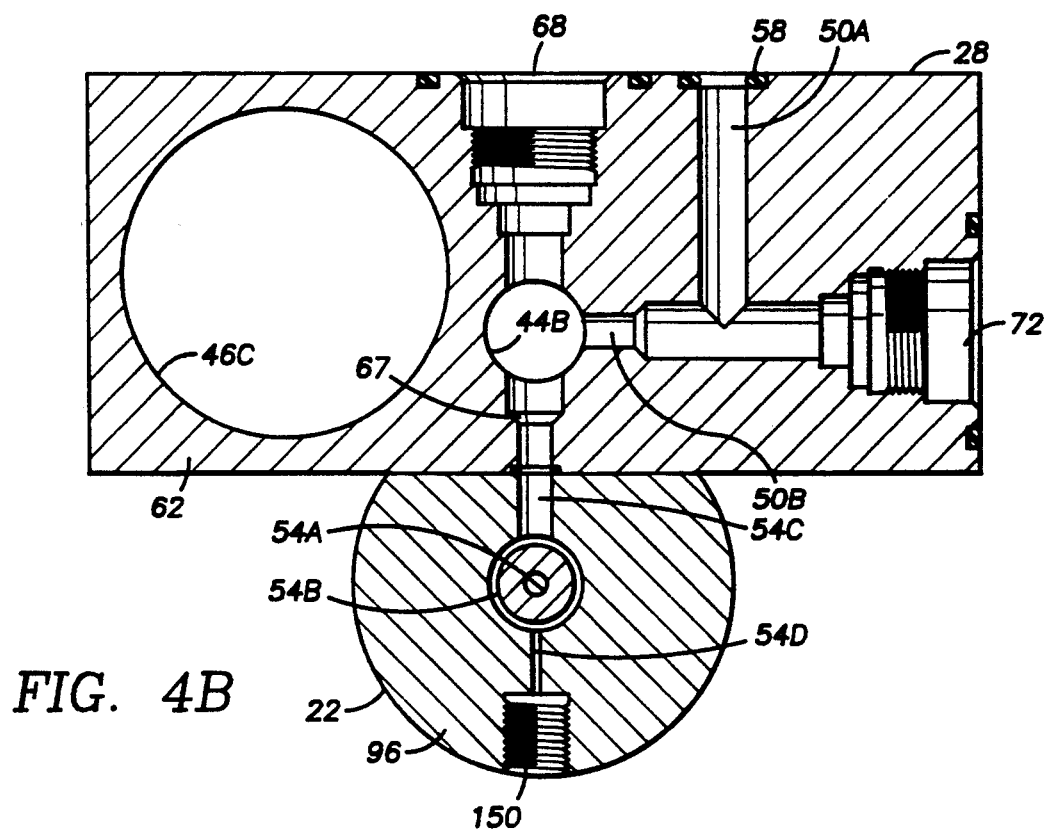
FIG. 4B is a sectional view along line B-B' of FIG. 4 through the probe-valve and large-tank-valve cavities.

FIG. 4B is a cross-sectional view along line B-B' of FIG. 4 through the lower portion of the manifold block 62. It shows a large-tank-valve cavity 72, the probe-valve cavity 68, the central manifold bore 44B, the probe inner-volume 54A, the probe outer-volume 54B, a probe channel 54C, a transducer channel 54D and two of the three parts of the large-tank chamber 50: a large-tank channel 50B and the large-tank inlet 50A sealed from the large-tank container (not shown) by the O-ring 58. A main body 50C (shown in FIG. 3) of the large-tank chamber 50 and the bottom portion 46C of the small-tank chamber 46 of the preferred embodiment contain copper tubing (not shown) to stabilize the temperature within the reservoir system 26 when the reservoir system 26 is filled or when the gas is being released from the reservoir system 26. This is noted by way of example and is not meant to restrict the invention to this means of temperature stabilization.

Improved test results are obtained if the temperature of the gas remains nearly constant during the test. When gas is compressed during the reservoir-fill phase, the temperature within the reservoir system 26 increases. When the gas expands, the temperature decreases. In the preferred embodiment permeameter 10, copper tubing is placed within the aluminum-walled large-tank chamber 50 and small-tank chamber 46 of the reservoir system 26 as described above. Because the copper tubing provides a large heat transfer area and has a large heat capacity, it acts as a temperature stabilizer. The copper tubing absorbs heat when gas is fed into the reservoir system 26 and the temperature of the gas remains relatively constant. When the gas is expanded into the probe chamber 54 and the core 16, the stored heat of the copper tubing restores the temperature lost due to the expansion.

The temperature also is affected by the material used for the manifold block 62 and the large-tank container 30. The preferred embodiment uses aluminum because of its heat transfer properties. Other materials such as brass can also be used.

Figure 4C:
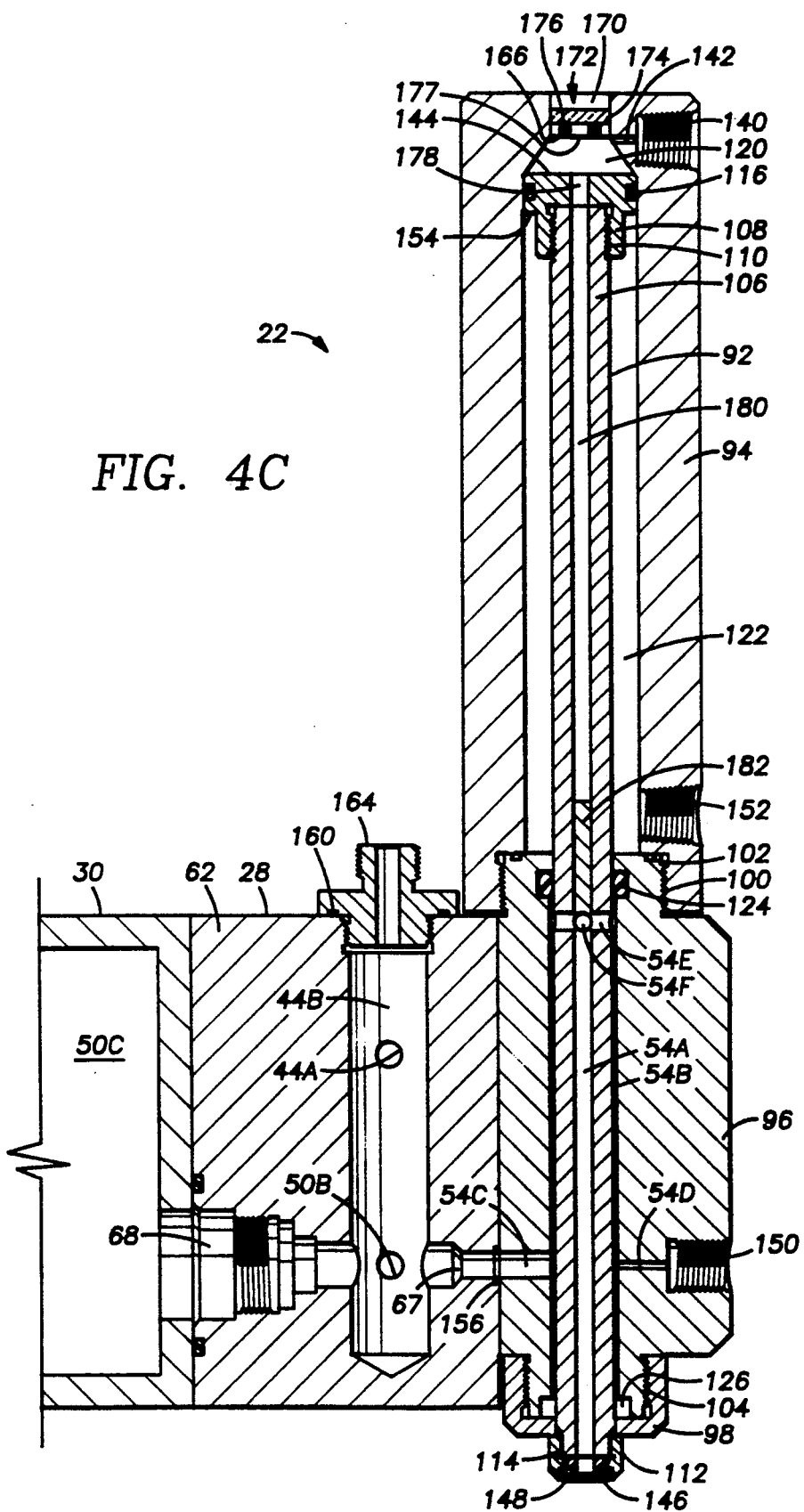
FIG. 4C is a sectional view along line C-C' of FIG. 4 through the axis of the probe.

FIG. 4C is a cross-sectional view along line C-C' of FIG. 4 through the manifold 28 and the axis of the probe 22. This figure illustrates all of the parts of the probe chamber 54: the probe inner-volume 54A, the probe outer-volume 54B, the probe channel 54C, the transducer channel 54D and probe crossbores 54E and 54F. The number of parts of the probe chamber 54 is shown by way of example and is not meant to limit the invention.

The probe 22 includes three primary parts: a probe housing 90, a probe assembly 92 and the probe chamber 54 (shown as 54A-F). The basic functions of the probe 22 are to form a seal with the core sample, act as a passageway of constant volume for pressurized gas between the manifold chamber 44 and the core sample and provide a sampling point for gas pressure measurements near the point of injection of the pressurized gas into the core sample.

The probe housing 90 consists of the upper-cylindrical housing 94, the lower-cylindrical housing 96 and a lower-housing cap 98. In the preferred embodiment, the upper and lower-cylindrical housings 94 and 96 are connected at a threaded connection 100 and sealed with an O-ring 102. Likewise, the lower-cylindrical housing 96 and the lower-housing cap 98 are joined at a threaded connection 104.

The probe assembly 92 includes the probe rod 106 joined at its top end to the operator piston 108 at a threaded connection 110 and joined at its bottom end to a probe tip 112 at a threaded connection 114. The probe assembly 92 moves up and down within a cylindrical space formed by the interior walls of the probe housing 90 and guided by the operator piston 108 in the upper-cylindrical housing 94 and by three O-rings: a first O-ring 116 in a groove in the outer surface of the operator piston 108 which forms an airtight seal between the upper chamber 120 and a lower chamber 122 of the upper-cylindrical housing 94, a second O-ring 124 located in a groove near the top of the inner surface of the lower-cylindrical housing 96 and a third O-ring 126 located in a groove near the bottom of the inner surface of the lower-cylindrical housing 96. The second O-ring 124 and the third O-ring 126 form the upper and lower seals, respectively, for the probe outer-volume 54B.

Once the operator has completed the initialization of the computer (explained above), the automated operation of the permeameter 10 begins. It should be noted that the probe 22 can be positioned manually, as explained in the description of a second preferred embodiment below, as well as automatically by the computer. In the automatic mode, the computer positions the probe 22 above the core sample 16 in the first channel 191 near the upper end 196 of the core sample 16 (shown in FIG. 1). The computer records the x and y coordinates of the position using inputs from the x-position sensor 32 and the y-position sensor 34.

To begin the reservoir-fill phase, the computer adjusts the valves (shown in FIG. 3) in the reservoir system 26 to the required positions: the probe valve 56 and the vent valve 60 are closed and the large-tank valve 52, the small-tank valve 48 and the fill valve 42 are opened. The three gas-containment chambers (described below) of the reservoir system 26 are then filled with gas from the pressurized gas supply 40 until the desired fill pressure within the reservoir system 26 is reached. The fill valve 42 then is closed. The preferred embodiment permeameter 10 uses a fill pressure of about 15 psig. The three gas-containment chambers of the reservoir system 26 are the manifold chamber 44 (shown as 44A-C), the small-tank chamber 46 (shown as 46A-C) and the large-tank chamber 50 (shown as 50A-C).

Because the probe valve 56 is closed, no pressurized gas reaches the probe chamber 54 and it will remain at atmospheric pressure during this reservoir-fill phase. The valves used in the preferred embodiment permeameter 10 are gas-activated poppet valves and take about 1/100 second to open. Nitrogen from the pressurized gas supply 40 is used in the preferred embodiment to activate the valves. The stroke of the vent valve 60 and the fill valve 42 is about 1/16 inch while the stroke of the large-tank valve 52, the small-tank valve 48 and the probe valve 56 is about 3/16 inch.

In the preferred embodiment permeameter 10, the end (not shown) of the probe valve 56 is shaped like a bullet. To close the probe valve 56, gas from the pressurized gas supply 40 is injected into the probe-valve cavity 68. The pressure of the gas pushes the probe valve 5 through the probe-valve cavity 68 (FIGS. 4A and 4C) and a captured O-ring (not shown), located around the probe valve 56 about 3/16 inch from the bullet-shaped end, presses against a seat 67 (FIGS. 4A and 4C) in the probe-valve cavity 68 providing an airtight seal between the probe chamber 54 and the manifold chamber 44. When the pressurized gas in the probe-valve cavity 68 is released, a spring (not shown) biases the probe valve 56 back to its opened position. The large-tank valve 52, the small-tank valve 48, the fill valve 42 and the vent valve 60 all operate in the same manner. In the preferred embodiment, valve bore caps (not shown) are screwed into position to hold the valves within their respective valve cavities. The large-tank container 30 covers the valve bore caps (not shown) of the vent valve 60, the fill valve 42 and the probe valve 56. The valve bore caps (not shown) for the small-tank and large tank chamber are covered by the right and left sides, respectively, of the manifold cover (not shown).

The computer then directs the probe assembly 92 to lower. In the preferred embodiment permeameter 10, the vertical movement of the probe assembly 92 is accomplished with pneumatic controls (not shown) which inject nitrogen from the pressurized gas supply 40 into a top inlet 140 (FIG. 4C) and through an inlet channel 142 to the upper chamber 120 of the probe 22. This exerts pressure on a top surface 144 of the operator piston 108 forcing the probe assembly 92 to move downward until a captured O-ring 146, located in a groove 148 in the probe tip 112 (FIG. 4C), engages the core sample 16 and forms a pressurized seal. As the operator piston 108 is forced downward, gas in the lower chamber 122 vents through a lower-chamber passageway 152.

The computer is now ready to take the necessary pressure-time measurements to determine pressure-decay parameters and the permeability of the core 16, as explained below. The probe valve 56 is opened allowing the pressurized gas to fill the probe chamber 54 and enter the core sample 16 through the probe tip 112. Because the probe chamber 54 is so small (about 4 cc) in comparison to the gas-containment chambers in the reservoir system 26 (about 860 cc), the drop in pressure is minimal as the gas expands into this additional chamber; and the resulting pressure in the probe chamber 54 will nearly equal the fill pressure of the reservoir system 26.

Using input from the pressure transducer 24, which measures the pressure of the gas within the transducer channel 54D (FIG. 4C) of the probe chamber 54, the computer records the fill pressure and starts an elapsed time clock (not shown).

The computer then waits for the first of two events to occur: either the pressure, as measured by the pressure transducer 24, drops to 92.5% of the fill pressure or 2.5 seconds elapse. When this first event occurs, the computer records the pressure and the elapsed time and resets the elapsed time clock.

The computer then waits for the first of the next two events to occur: either the pressure within the probe chamber 54 drops to 50% of the fill pressure or 2.5 seconds elapse on the reset timer. When this first event occurs, the computer records the pressure and time. The computer then selects the preferred volume of pressurized gas to be used to determine the permeability of the core sample 16 at this test position by comparing these two sets of pressure-time values, or their resultant pressure decay rate, to predetermined threshold values stored in the computer.

In the preferred embodiment, four different volumes can be selected by the computer (FIG. 3). For a high permeability core sample (fastest pressure decay rate), the computer selects the largest volume: the large-tank chamber 50 (shown as 50A-C), the small-tank chamber 46 (shown as 46A-C), the manifold chamber 44 (shown as 44A-C) and the probe chamber 54. For the next lower permeability range, the computer selects the next smallest volume by closing the large-tank valve 52 leaving the small-tank chamber 46, the manifold chamber 44 and the probe chamber 54. For the next lower permeability range, the computer selects the next smallest volume by closing the large-tank valve 52 and the small-tank valve 48 leaving the manifold chamber 44 and the probe chamber 54. For the lowest permeability range (slowest pressure decay rate), the computer will select the smallest gas-containment chamber, the probe chamber 54, by closing the large-tank valve 52, the small-tank valve 48 and the probe valve 56.

A set of maximum test time intervals corresponding to varying pressure decay rates is stored in the computer and can be modified by the operator. The maximum test time interval spans the amount of time required for the desired pressure transient to occur. In the preferred embodiment, the maximum time of 24 seconds is used for core samples with permeability greater than about 0.1 md. For core samples with lower permeabilities, the preferred maximum test time interval is about 30 seconds. The time required for the pressure transient to occur is directly proportional to the cumulative volume of pressurized gas in the reservoir system 26 and the probe chamber 54 that is used for the test, the permeability of the core sample 16 and an inner diameter 149 (shown in FIG. 3) of the seal formed between the O-ring 146 and the core sample 16. The time for a pressure transient in the preferred embodiment is anticipated to range from 4 to 24 seconds for permeabilities greater than 0.1 md and from 24 to 35 seconds for permeabilities of 0.1 to 0.001 md.

Figure 5A:
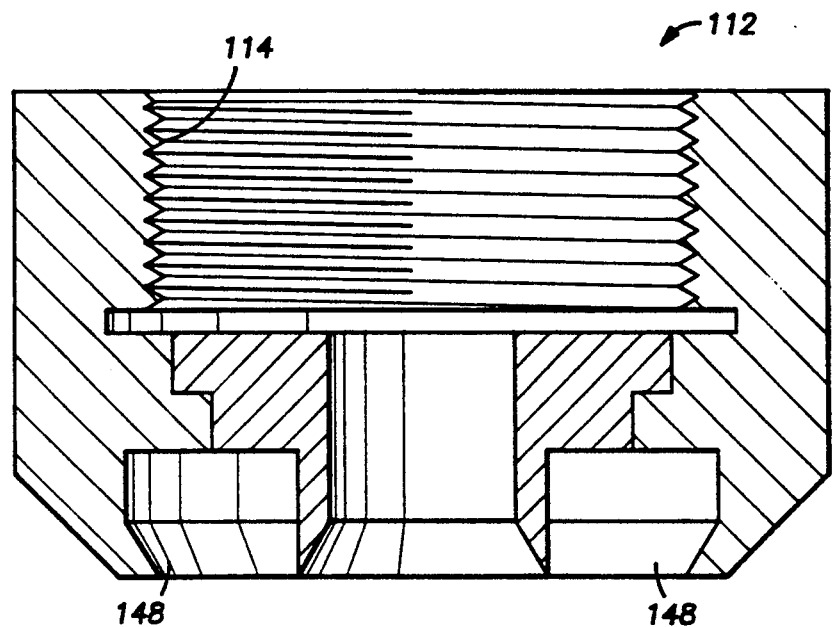
FIG. 5A is a sectional view of the probe tip used in the preferred embodiment of the invention.
Figure 5B:
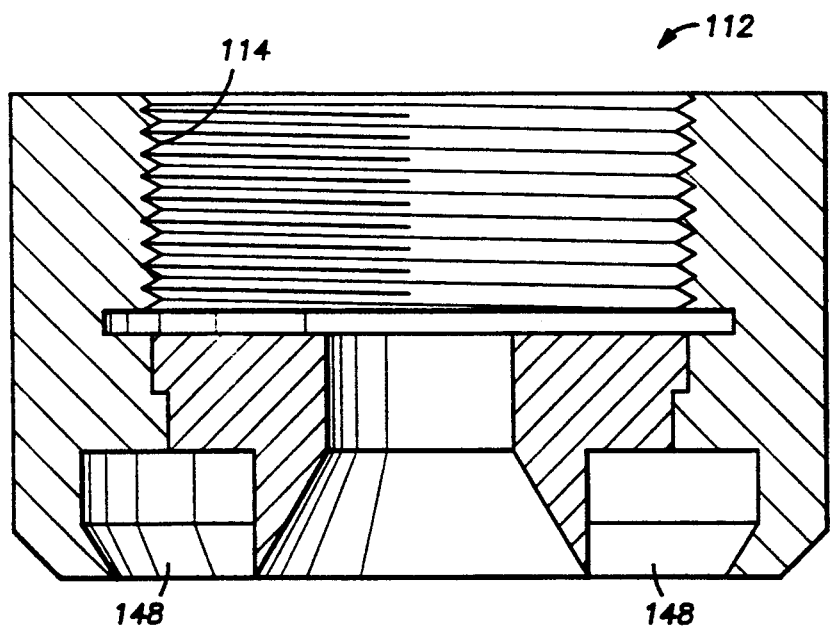
FIG. 5B is a sectional view of an optional probe tip for use with low permeability core samples.

If very low permeabilities are anticipated for an entire set of measurements, the time for the pressure transient can be reduced and/or the lower permeability limit can be extended by increasing the inner diameter 149 (FIG. 3) of the seal formed between the O-ring 146 and the core sample 16. One way to increase the inner diameter 149 of the seal is to use a different probe cap 112 such as the one shown in FIG. 5B.

Once the computer has adjusted the volume of the reservoir by closing the appropriate valves, the pressure and time values are recorded. The pressure transducer 24, in the preferred embodiment, then samples the pressure within the transducer channel 54D of the probe 22 at approximately 100 times per second. The computer uses a series of nineteen predetermined pressure thresholds. As the pressure reading reaches a threshold, the computer records the pressure and the corresponding time interval. As soon as the lowest pressure threshold (0.15 psig in the preferred embodiment) is reached or the maximum test time has elapsed, whichever occurs first, the final pressure measurement and time are recorded to provide a minimum of two pairs of pressure-time measurements for this measurement position. The computer then closes the probe valve 56 and opens the large-tank valve 52, the small-tank valve 48 and the fill valve 42 to refill the reservoir system 26 for the next test.

During this reservoir-fill phase, the computer raises the probe assembly 92 by venting the pressurized gas from the upper chamber 120 of the probe 22 through the inlet channel 142 and the top inlet 140 and injecting gas from the pressurized gas supply 40 through the lower-chamber passageway 152 into the lower chamber 122. The pressure of the gas against a bottom surface 154 of the operator piston 108 forces the operator piston 108 upwards resulting in the upward movement of the probe assembly 92 thus breaking the pressure seal between the O-ring 146 and the surface 200 of the core sample 16.

While raising the probe assembly 92, the computer determines the permeability of the core sample 16 at the measurement point. Instead of directly measuring the flowrate as is done in the steady-state technique of the prior art, the transient pressure-decay technique of the present invention uses the known, adjusted reservoir volume and the pressure-decay rates derived from the measured pressure-time values to calculate instantaneous flowrate functions for pairs of pressure-time measurements as follows:

$$y[n] = \frac{V_T(\ln(p[n-1]/p[n]))}{(t[n] - t[n-1])} \quad (1)$$

where, $V_T$ is the adjusted reservoir volume, $p[n]$ is the second of the pair of pressure measurements, $p[n-1]$ is the first of the pair of pressure measurements and $(t[n]-t[n-1])$ is the time interval between the two pressure measurements.

The instantaneous flowrate function ($y[n]$) is valid at the midpoint of the logarithmic pressure range which is the geometric mean pressure of the pressure-time interval from which $y[n]$ was calculated. Because the gas vents from the core sample 16 at atmospheric pressure and the gas pressure readings from the pressure transducer 24 are measured as psig in the preferred embodiment, a pressure measurement represents an instantaneous pressure drop in the core sample through which the gas is flowing. Therefore, for each instantaneous flowrate function ($y[n]$), the corresponding instantaneous pressure drop ($p_g[n]$) is this geometric mean pressure, which is calculated as follows:

$$p_g[n] = ((p[n])(p[n-1]))^{\frac{1}{2}} \quad (2)$$

Several pairs of instantaneous flowrate functions and pressure drop values are thus obtained.

The instantaneous flowrate functions can also be expressed by an equivalent relationship as:

$$y[n] = \frac{(q[n])(p_g[n] + p_a)}{p_g[n]} \quad (3)$$

where, q is the instantaneous volumetric flowrate of the gas entering the core sample, $p_g$ is the instantaneous pressure drop and $p_a$ is the atmospheric pressure.

Because the pressure of the gas being injected into the core sample 16 progressively decays with time, the average flow velocity, the average gas density and the mean pore pressure all decrease correspondingly. Consequently, the Klinkenberg (gas slippage-corrected) permeability, the Klinkenberg slip factor and the Forchheimer inertial resistance factor can all be determined from the multiplicity of flow conditions, using the appropriate integrated form of the Forchheimer flow equation. These parameters can all be determined from a single pressure transient calculated from the pairs of pressure-time values recorded at the measurement position as described above.

After determining the viscosity of the nitrogen used in the preferred embodiment:

$$\mu = 0.01652 + 0.0000468T, \quad (4)$$

where, T = the ambient temperature in degrees Celsius, a geometric factor ($G_o r_i$) is selected. The geometric factor can be obtained by calibrating a suite of homogeneous core samples that have known values of Klinkenberg permeability, preferably extrapolated to zero confining stress, or the geometric factor can be calculated theoretically from an inside ($r_i$) and an outside radius ($r_o$) of the portion of the O-ring 146 which is in sealed communication with the core sample 16 and values of $G_o$, where $G_o$ is a function of the ratio ($r_o/r_i$) of the outside to inside radius, as presented by D. J. Goggin, R. L. Thrasher & L. W. Lake in "A Theoretical & Experimental Analysis of Mini-Permeameter Response Including Gas Slippage & High Velocity Flow Effects" (In Situ, Vol. 12, 1988, at page 79).

The geometry of gas flowing from the probe 22 through the core sample 16 is complex and the flow path lengths vary considerably. The shortest flow path is the radial path just below the surface of the core 16, from inside the O-ring 146 to its outer radius, exiting from the top surface of the core sample 16 just beyond this radius. The longest flow path is perpendicular to the surface of the core 16, from the probe 22 through the thickness of the core sample 16. Because of the large variation in the lengths of the flow paths, flow velocities also vary. These variations are accentuated by permeability heterogeneity. Consequently, except in fairly low-permeability samples, permeability measurements are susceptible to non-negligible inertial flow resistance even with fairly low pressures in the probe 22.

In principle, it is possible to account for inertial flow resistance from the multiple measurements made in the transient pressure-decay method. For measurements made primarily on highly non-homogeneous rock, however, the computations are more robust if allowance is made for core samples in which Darcy's law does not apply across the full measurement range. To determine if Darcy's law applies, coefficients obtained from a least-squares curve fit of selected pairs of instantaneous flowrate functions and pressure drop values are analyzed. When few pairs of data are available, a linear least-squares curve fit is used to obtain coefficients $A_0$ (intercept) and $A$ (slope) from the following relationship:

$$y[n] = A_0 + A_1 p_g[n]. \quad (5)$$

Darcy's law applies throughout the measurement range if both $A_0$ and $A_1$ are greater than zero.

When more data are available, the last six pairs of y and $p_g$ values, which represent the lowest pressure measurements, are used to determine coefficients $A_0$, $A_1$ and $A_2$ from a second-order equation based on the following relationship:

$$y[n] = A_0 + A_1 p_g[n] + A_2 p_g[n]^2. \quad (6)$$

If both $A_0$ and $A_1$ are greater than zero and $A_2$ is equal to zero, Darcy's law applies across the full range of the six pairs of data.

When Darcy's law does apply, the slip-corrected Klinkenberg permeability ($k_\infty$) and the Klinkenberg slip factor (b) can be calculated directly from the coefficients $A_0$ and $A_1$ derived from the pressure-time measurements as follows:

$$k_\infty = \frac{29392\, \mu\, A_1}{G_o r_i} \text{ and} \quad (7)$$

$$b = \frac{A_0}{2 A_1} - p_a \quad (8)$$

where $\mu$ is the viscosity of the gas, $G_o r_i$ is the selected geometric factor and $p_a$ is the atmospheric pressure.

If the data indicate that Darcy's law does not apply, an instantaneous flowrate function ($y^*$) is obtained from the second-order least-squares relationship, as shown in Equation (6) above, corresponding to the minimal instantaneous pressure drop value ($p_g^*$). If the minimal $p_g^*$ is less than a selected threshold, the $Y^*$ is extrapolated to correspond to a zero $p_g^*$. At a $p_g^*$ value of zero, the corresponding $y^*$ has a value of $A_0$. In the case of a very low permeability sample where only a single pair of y and $p_g$ values are obtained, $y^*$ is given a value of y[1] and $p_g^*$ is given a value of $p_g[1]$.

Although the slip factor (b) cannot be directly obtained from the measurements in the higher permeability core samples where Darcy's law does not apply, the slip factor will be fairly small and can be obtained from a correlation with adequate accuracy to permit calculation of the Klinkenberg permeability. Any slip factor that is obtained from a correlation is denoted below as $b^*$.

To obtain a slip factor from a correlation, an initial estimation of the slip factor ($b^*$) is made and then the Klinkenberg permeability ($k_\infty$) is calculated as follows:

$$k_\infty = \frac{29392\, \mu\, y^*}{(G_o r_i)(p_g^* + 2p_a + 2b^*)} \quad (9)$$

where $\mu$ is the viscosity of the gas, $p_g^*$ is a selected instantaneous pressure drop value, $y^*$ is the corresponding instantaneous flowrate function, $G_o r_i$ is the geometric factor and p is the atmospheric pressure.

Using the calculated value of $k_\infty$, an improved estimate of the slip factor ($b^*$) is then obtained from:

$$b^* = 6.9\, k_\infty - 0.382 \quad (10)$$

The new slip factor ($b^*$) then is inserted into Equation (9) and the process is repeated until the change in the slip factor ($b^*$), from one iteration to the next, is less than 0.1 psi.

Then the effective gas permeability (ke), also known as the non-slip-corrected gas permeability, is calculated as follows:

$$k_G = \frac{29392\, \mu\, y^*}{(G_o r_i)(p_g^* + 2p_a)} \quad (11)$$

where $\mu$ is the viscosity of the gas, $p_g^*$ is the selected instantaneous pressure drop, $y^*$ is the corresponding instantaneous flowrate function, $G_o r_i$ is the geometric factor and p is the atmospheric pressure.

As the reservoir-fill phase and calculations are being done, the computer positions the probe 22 at the next measurement position by moving the y-carriage 20 (FIG. 1) containing the probe 22 along the y-rails 36 and/or by moving the x-carriage 18 containing the y-carriage 20 along the x-rails 38. The next measurement position is determined by the computer and is either the next position (one measurement interval) along the core sample 16 in the first channel 191 or, if the end of this core sample 16 has been tested, the initial position of the next core sample 16 located in a second channel 192 of the core rack 14. Manual positioning by the operator is also possible. The process is repeated until measurements are taken and permeabilities are calculated for all desired measurement points in core samples 16 in the core rack 14.

SECOND PREFERRED EMBODIMENT

Figures 6A, 6B:
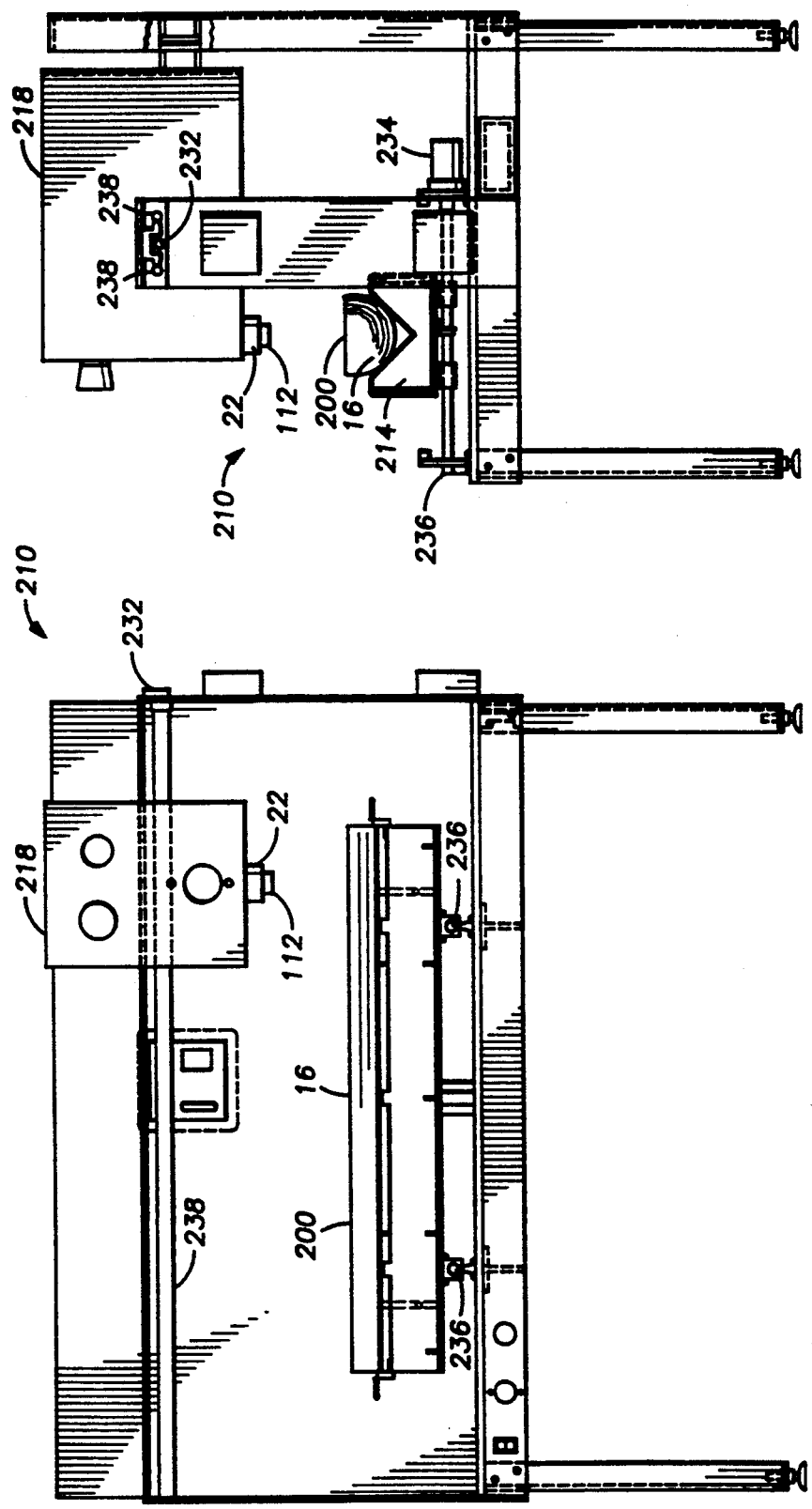
FIGS. 6A and 6B are front and side views, respectively, of a second preferred embodiment of the invention.

FIGS. 6A and 6B show the front end and side views, respectively, of a second preferred embodiment permeameter 210. The physical positioning of the probe 22 along y-rails 236 and x-rails 238 is done manually by the operator. The sensing of the position of the probe 2 is done automatically using positioning sensors (such as those manufactured by Temposonics) that continuously measure the position of the probe 22 with respect to the reference point (leading edge of the core sample along the reference depth marking). The permeameter 210 uses an x-linear-displacement transducer 232 and a y-linear-displacement transducer 234 for the positioning sensors but other sensors can be used. The vertical movement of the probe 22 to engage the core 16, the operation of the valves in the reservoir system, the pressure-time readings and the calculations are done automatically by the computer as explained above for the permeameter 10.

The operator places the core sample 16 on a core rack 214 with the upper end (not shown) of the core sample 16 at the left end of the core rack 214 and with the slabbed surface 200 facing upwards towards the probe 22. The operator then initializes the computer (not shown) with the reference depth (explained above) of the core sample 16.

With the aid of a laser light (as explained above), the operator positions the probe 22 above the core sample 16. The x-carriage 218 is moved along the x-rails 238 until the probe 22 is aligned on the x axis directly above the reference depth line on the core sample 16. The y-carriage, which is the core rack 214 in this embodiment, is then moved forward and backwards along the y-rails 236 until the probe 22 is over the leading edge (towards the operator) of the reference depth line. The operator then presses the button (not shown) and the computer records the x and y positions of the reference depth line using input from the x-linear-displacement transducer 232 and the y-linear-displacement transducer 234.

The operator now manually positions the probe 22 above a spot on the core sample 16 to be tested. When the probe 22 is properly positioned, the operator pushes the button to start the automated procedure. The computer records the x and y position of the test point and then lowers the probe 22 until a seal is formed between the O-ring 146 in the probe tip 112 and continues with the automated phase as described above for the permeameter 10.

When the pressure-time measurements and permeability calculations are completed for the measurement point, the computer automatically raises the probe 22 and goes through the reservoir-fill phase. The computer then waits for the operator to manually position the probe 22 above the next desired test point and the procedure is repeated.

While the foregoing has described two preferred embodiments of the present invention, it is to be understood that various modifications or changes may be made without departing from the scope of the invention as set forth in the appended claims.

What is claimed is:

1. A transient, pressure-decay method of determining permeability of a core sample, comprising the steps of:
    (a) positioning a probe in sealed communication with the core sample;
    (b) injecting pressurized gas through the probe into the core sample from a reservoir having a known volume that contains the pressurized gas, whereby the pressurized gas diffuses through the core sample in a modified hemispherical pattern;
    (c) measuring at selected intervals the pressure (p) of the gas as it flows through the probe into the core sample and the time (t) between the pressure measurement;
    (d) calculating instantaneous pressure-decay parameters based on the pressure-time measurements of step (c); and
    (e) determining the permeability of the core sample from the instanteous pressure-decay parameters of step (d).

2. The method of claim 1, wherein the positioning step further comprises the step of shining a laser light through the probe onto the core sample to facilitate the positioning of the probe on a selected measurement point on the core sample.

3. The method of claim 1, wherein the step of injecting pressurized gas into the core sample comprises the steps of:
    (a) estimating the permeability of the core sample;
    (b) adjusting the volume of a reservoir of pressurized gas until the volume is approximately equal to a preferred volume based on the estimated permeability of the core sample; and
    (c) injecting the pressurized gas from the adjusted volume of the reservoir through the probe into the core sample.

4. The method of claim 3, wherein the permeability estimation step comprises:
    (a) making a first measurement of the pressure of the gas flowing into the core sample and the time of the measurement, wherein the first measurement is made when the gas begins flowing into the core sample;
    (b) making a second measurement of the pressure of the gas flowing into the core sample and the time of the measurement, wherein the second measurement is made when the first of two events occurs, wherein one of the events is a drop in pressure of the gas to a selected level and the other event is the passage of a selected amount of time since the first measurement;
    (c) making a third measurement of the pressure of the gas flowing into the core sample and the time of the measurement, wherein the third measurement is made when the first of two events occurs, wherein one of the events is a drop in pressure of the gas to a selected level and the other event is the passage of a selected amount of time since the second measurement; and
    (d) estimating the permeability of the core sample based on the pressure measurements and the elapsed time between the pressure measurements.

5. The method of claim 3, wherein the reservoir comprises a plurality of chambers having valve means for adjusting the volume of the reservoir, wherein activating a valve means for a chamber closes off the chamber and reduces the volume of the reservoir by an amount equal to the volume of that chamber.

6. The method of claim 5, further comprising the step of calibrating the volumes of the chambers in the reservoir.

7. The method of claim 5, wherein the pressurized gas passes from the reservoir through a chamber of the probe into the core sample, said probe chamber having a known volume, wherein:
    (a) said reservoir comprises three chambers having valve means,
        (i) said first chamber having a volume of about five times the volume of the probe chamber;
        (ii) said second chamber having a volume of about six times the volume of the first chamber; and
        (iii) said third chamber having a volume of about six times the volume of the second chamber; and
    (b) wherein the volume adjusting step comprises the steps of:
        (i) activating a first chamber valve means if the estimated permeability is greater than a first permeability threshold;
        (ii) activating a second chamber valve means if the estimated permeability is greater than a second permeability threshold; and
        (iii) activating a third chamber valve means if the permeability is greater than a third permeability threshold.

8. The method of claim 1, wherein the measurement step comprises:
    (a) measuring the pressure of the gas in the probe at a selected frequency;
    (b) comparing the pressure measurements with a series of selected pressure thresholds;
    (c) recording the pressure measurement and the time of the measurement whenever the pressure reaches one of the selected pressure thresholds; and
    (d) continuing steps (a)-(c) until the first of two events occur, wherein one of the events is the pressure reaching the last of the selected pressure thresholds and the other event is the passage of a selected maximum time interval.

9. The method of claim 1, wherein the instantaneous pressure-decay parameters calculation step comprises the steps of:
(a) calculating instantaneous flowrate functions (y) for pairs of pressure-time measurements, wherein the calculation comprises:

$$y[n] = \frac{V_T(\ln(p[n-1]/p[n]))}{(t[n] - t[n-1])}$$

where
$V_t$ = the volume of pressurized gas in the reservoir,
p[n] = the second of a pair of pressure measurements,
p[n-1] = the first of the pair of pressure measurements and
(t[n]-t[n-1]) = the time interval between the two pressure measurements; and
(b) calculating corresponding instantaneous pressure drops ($p_g$);
wherein the calculation comprises:

$$p_g[n] = ((p[n])(p[n-1]))^{\frac{1}{2}}$$

10. The method of claim 9, wherein the permeability determination step comprises the steps of:
(a) calculating the viscosity ($\mu$) of the gas in the reservoir;
(b) determining a geometric factor ($G_o r_i$) based on the geometry of the seal formed between the probe and the core sample;
(c) curve fitting selected pairs of instantaneous flowrate functions (y) and corresponding pressure drop values ($p_g$) to determine coefficients $A_0$, $A_1$ and $A_2$;
(d) calculating the Klinkenberg permeability ($k_\infty$), wherein said calculation comprises:

$$k_\infty = \frac{29392 \, \mu \, A_1}{G_o r_i};$$

(e) calculating the Klinkenberg slip factor (b), wherein said calculation comprises:

$$b = \frac{A_0}{2A_1} - p_a$$

where, $p_a$ is the atmospheric pressure; and
(f) calculating the effective permeability ($k_G$) of the core sample, wherein said calculation comprises:

$$k_G = \frac{29392 \, \mu \, y}{(G_o r_i)(p_g + 2p_a)}$$

where,
$p_g$ = an instantaneous pressure drop value and
y = the corresponding instantaneous flowrate function.

11. The method of claim 10, further comprising the step of eliminating inertial flow resistance effects for core samples having high permeability, wherein the elimination step comprises:
(a) selecting the smallest instantaneous pressure drop value ($p_g^*$) from the plurality of $p_g$ values;
(b) calculating an instantaneous flowrate function ($y^*$) based on the selected $p_g^*$ value, wherein said calculation comprises:

$$y^* = A_0 + A_1 p_g^* + A_2(p_g^*)^2;$$

(c) extrapolating $y^*$ to correspond to a $p_g^*$ of value zero if the selected $p_g^*$ value is less than a selected threshold;
(d) estimating a first value for the Klinkenberg slip factor ($b^*$);
(e) calculating the Klinkenberg permeability ($k_\infty$) based on the slip factor ($b^*$), wherein the calculation comprises:

$$k_\infty = \frac{29392 \, \mu \, y^*}{(G_o r_i)(p_g^* + 2p_a + 2b^*)};$$

(f) calculating an improved value of the Klinkenberg slip factor ($b^*$) based on the calculated Klinkenberg permeability ($k_\infty$) of step (e), wherein said calculation comprises:

$$b^* = 6.9 \, k_\infty - 0.382;$$

(g) reiterating the Klinkenberg permeability and slip factor calculation steps (e) and (f) until the change in the slip factor ($b^*$) from the previous iteration is within a selected tolerance; and
(h) calculating the effective permeability ($k_G$) based on the $p_g^*$ and $y^*$ values, wherein the calculation comprises:

$$k_G = \frac{29392 \, \mu \, y^*}{(G_o r_i)(p_g^* + 2p_a)}.$$

12. The method of claim 1, further comprising the step of allowing the temperature of the gas within the reservoir to stabilize to ambient temperature prior to measuring the pressure of the gas.

13. The method of claim 12, wherein the temperature stabilization step is facilitated by placing a plurality of copper tubes in the reservoir.

14. An apparatus for determining the permeability of a core sample using a transient, pressure-decay technique, comprising:
(a) a reservoir for dispensing pressurized gas from a known volume of pressurized gas;
(b) a probe in sealed communication with the reservoir and the core sample for passage of the pressurized gas from the reservoir through the probe into the core sample, whereby the pressurized gas diffuses through the core sample in a modified hemispherical pattern;
(c) means for measuring the pressure of the gas as it passes through the probe,
(d) means for measuring the elapsed time between the pressure measurements; and
(e) means for calculating pressure-decay parameters from the pressure-time measurements and calculating the permeability of the core sample based on the pressure-decay parameters.

15. The apparatus of claim 14, wherein the probe comprises an input end in sealed communication with the reservoir, an output end in sealed communication with the core sample and a probe chamber of known volume connecting said input end to said output end, said probe chamber in pressure communication with the pressure measuring means.

16. The apparatus of claim 15, further comprising means for positioning the output end of the probe in sealed communication with a selected measurement point on the core sample.

17. The apparatus of claim 16, wherein the positioning means comprises:
   (a) a first carriage in which the probe is movably seated, said first carriage movably mounted above the core sample, wherein the probe is positioned laterally by moving said first carriage along the core sample until the probe is aligned with a first coordinate of the measurement point;
   (b) a second carriage in which the core sample is held, wherein the core sample is aligned by moving said second carriage backward or forward until a second coordinate of the measurement point is positioned beneath the probe; and
   (c) means for moving the probe after it is aligned with the first and second coordinates between a rest position within the first carriage and a measurement position where the output end of the probe is in sealed communication with the measurement point on the core sample.

18. The apparatus of claim 16, wherein the positioning means comprises:
   (a) a first carriage in which the probe is movably seated;
   (b) a second carriage in which the first carriage is movably mounted, said second carriage is movably positioned above the core sample, wherein the probe is aligned laterally by moving said second carriage along the core sample until the probe is aligned with a first coordinate of the measurement point and the probe is aligned with a second coordinate of the measurement point by moving the first carriage backward or forward until the second coordinate is below the probe; and
   (c) means for moving the probe after it is aligned with the first and second coordinates of the measurement point between a rest position within the first carriage and a measurement position where the output end of the probe is in sealed communication with the measurement point on the core sample.

19. The apparatus of claim 16, wherein the positioning means further comprises laser-light guiding means, wherein a laser light is illuminated such that the light shines from the output end of the probe onto the core sample at a position aligned with the center of the output end of the probe.

20. The apparatus of claim 16, further comprising detecting means for determining the position of the probe relative to a reference position.

21. The apparatus of claim 15, wherein the reservoir comprises a plurality of chambers of known volumes connected to the probe chamber by a plurality of valve means, wherein the opening and closing of a valve means for a chamber respectively increases and decreases the volume of pressurized gas in the reservoir that is in pressure communication with the probe chamber.

22. The apparatus of claim 21, wherein the reservoir further comprises calibrating means for adjusting the volumes of the chambers.

23. The apparatus of claim 21, wherein the chambers comprise:
   (a) a first chamber having a volume larger than the volume of the probe chamber, wherein a first valve means provides communication between the first chamber and the probe chamber;
   (b) a second chamber having a volume larger than the volume of the first chamber, wherein a second valve means provides communication between the second chamber and the probe chamber; and
   (c) a third chamber having a volume larger than the second volume, wherein a third valve means provides communication between the third chamber and the probe chamber.

24. The apparatus of claim 23, wherein the probe chamber has a volume of approximately four cubic centimeters, the first chamber has a volume of approximately twenty cubic centimeters, the second chamber has a volume of approximately one hundred twenty cubic centimeters and the third chamber has a volume of approximately seven hundred twenty cubic centimeters.

25. The apparatus of claim 14, wherein the reservoir contains a plurality of copper tubes to facilitate the stabilization of the temperature of the gas within the reservoir.

* * * * *